(12) United States Patent
Bernard et al.

(10) Patent No.: US 6,541,286 B1
(45) Date of Patent: Apr. 1, 2003

(54) IMAGING OF INTEGRATED CIRCUIT INTERCONNECTS

(75) Inventors: Joffre F. Bernard, Redwood City, CA (US); Minh Quoc Tran, Milpitas, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/894,284

(22) Filed: Jun. 27, 2001

(51) Int. Cl.[7] ............................................... G01R 31/26
(52) U.S. Cl. ............................. 438/14; 438/16; 438/17; 438/623; 438/624; 438/625; 438/626; 438/627; 438/628
(58) Field of Search ............................. 438/14, 16, 17, 438/622, 623, 624, 625, 626, 627, 628

(56) References Cited

U.S. PATENT DOCUMENTS

| | | | | |
|---|---|---|---|---|
| 4,332,833 A | * | 6/1982 | Aspnes et al. | |
| 6,002,790 A | * | 12/1999 | Horvath et al. | |
| 6,066,561 A | * | 5/2000 | Kumar et al. | |
| 6,191,855 B1 | * | 2/2001 | Maris | |
| 6,351,516 B1 | * | 2/2002 | Mazor et al. | |

* cited by examiner

*Primary Examiner*—Long Pham
(74) *Attorney, Agent, or Firm*—Mikio Ishimaru

(57) ABSTRACT

A method is provided for X-ray imaging and analyzing grain boundaries, nodules or extrusions, voids, and separations or delaminations in conductive layers under dielectric capping layers in integrated circuit interconnects.

14 Claims, 2 Drawing Sheets

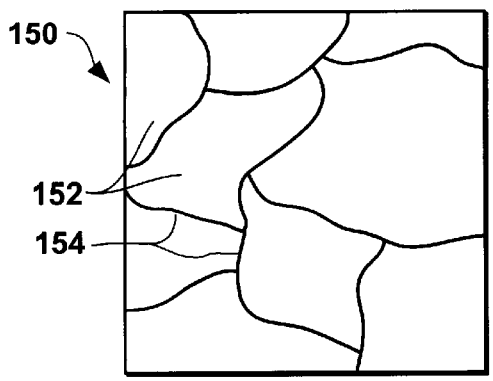
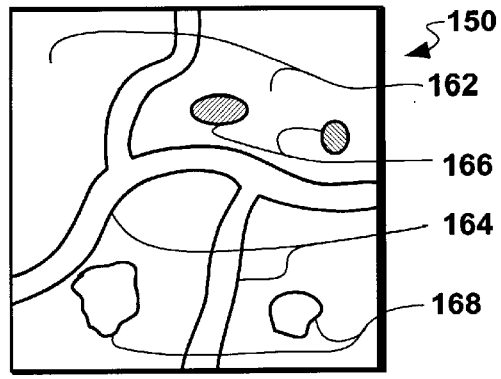
FIG. 3 (PRIOR ART)          FIG. 4 (PRIOR ART)
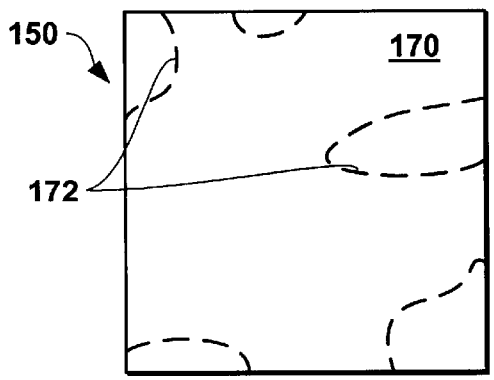
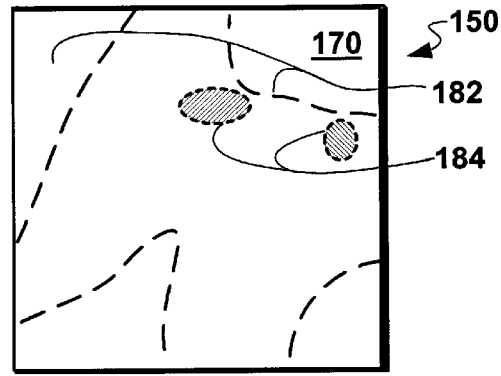
FIG. 5 (PRIOR ART)          FIG. 6 (PRIOR ART)
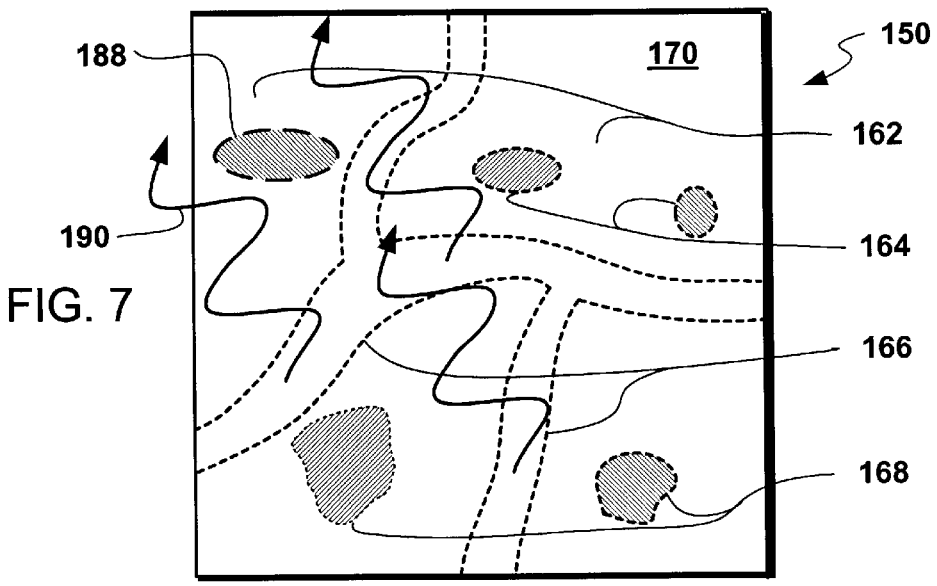
FIG. 7

IMAGING OF INTEGRATED CIRCUIT INTERCONNECTS

TECHNICAL FIELD

The present invention relates generally to semiconductor analysis and more particularly to a method for imaging and monitoring grain boundaries, nodules or extrusions, voids, and separations or delaminations in conductive layers under dielectric capping layers in integrated circuit interconnects.

BACKGROUND ART

In the manufacture of integrated circuits, after the individual devices such as the transistors have been fabricated in and on the semiconductor substrate, they must be connected together to perform the desired circuit functions. This interconnection process is generally called "metallization" and is performed using a number of different photolithographic, deposition, and removal techniques.

In one interconnection process, which is called a "dual damascene" technique, two channels of conductor materials are separated by interlayer dielectric layers in vertically separated planes perpendicular to each other and interconnected by a vertical connection, or "via", at their closest point. The dual damascene technique is performed over the individual devices which are in a device dielectric layer with the gate and source/drain contacts extending up through the device dielectric layer to contact one or more channels in a first channel dielectric layer.

The first channel formation of the dual damascene process starts with the deposition of a thin first channel stop layer. The first channel stop layer is an etch stop layer which is subject to a photolithographic processing step which involves deposition, patterning, exposure, and development of a photoresist, and an anisotropic etching step through the patterned photoresist to provide openings to the device contacts. The photoresist is then stripped. A first channel dielectric layer is formed on the first channel stop layer. Where the first channel dielectric layer is of an oxide material, such as silicon oxide ($SiO_2$), the first channel stop layer is a nitride, such as silicon nitride (SiN), so the two layers can be selectively etched.

The first channel dielectric layer is then subject to further photolithographic process and etching steps to form first channel openings in the pattern of the first channels. The photoresist is then stripped.

An optional thin adhesion layer is deposited on the first channel dielectric layer and lines the first channel openings to ensure good adhesion of subsequently deposited material to the first channel dielectric layer. Adhesion layers for copper (Cu) conductor materials are composed of compounds such as tantalum nitride (TaN), titanium nitride (TiN), or tungsten nitride (WN).

These nitride compounds have good adhesion to the dielectric materials and provide good barrier resistance to the diffusion of copper from the copper conductor materials to the dielectric material. High barrier resistance is necessary with conductor materials such as copper to prevent diffusion of subsequently deposited copper into the dielectric layer, which can cause short circuits in the integrated circuit.

However, these nitride compounds also have relatively poor adhesion to copper and relatively high electrical resistance.

Because of the drawbacks, pure refractory metals such as tantalum (Ta), titanium (Ti), or tungsten (W) are deposited on the adhesion layer to line the adhesion layer in the first channel openings. The refractory metals are good barrier materials, have lower electrical resistance than their nitrides, and have good adhesion to copper.

In some cases, the barrier material has sufficient adhesion to the dielectric material that the adhesion layer is not required, and in other cases, the adhesion and barrier material become integral. The adhesion and barrier layers are often collectively referred to as a "barrier" layer herein.

For conductor materials such as copper, which are deposited by electroplating, a seed layer is deposited on the barrier layer and lines the barrier layer in the first channel openings to act as an electrode for the electroplating process. Processes such as electroless, physical vapor, and chemical vapor deposition are used to deposit the seed layer.

A first conductor material is deposited on the seed layer and fills the first channel opening. The first conductor material and the seed layer generally become integral, and are often collectively referred to as the conductor core when discussing the main current-carrying portion of the channels.

A chemical-mechanical polishing (CMP) process is then used to remove the first conductor material, the seed layer, and the barrier layer above the first channel dielectric layer to form the first channels. When a layer is placed over the first channels as a final layer, it is called a "capping" layer and a "single" damascene process is completed. When the layer is processed further for placement of additional channels over it, the layer is a via stop layer.

The via formation of the dual damascene process starts with the deposition of a thin via stop layer over the first channels and the first channel dielectric layer. The via stop layer is an etch stop layer which is subject to photolithographic processing and anisotropic etching steps to provide openings to the first channels. The photoresist is then stripped.

A via dielectric layer is formed on the via stop layer. Again, where the via dielectric layer is of an oxide material, such as silicon oxide, the via stop layer is a nitride, such as silicon nitride, so the two layers can be selectively etched. The via dielectric layer is then subject to further photolithographic process and etching steps to form the pattern of the vias. The photoresist is then stripped.

A second channel dielectric layer is formed on the via dielectric layer. Again, where the second channel dielectric layer is of an oxide material, such as silicon oxide, the via stop layer is a nitride, such as silicon nitride, so the two layers can be selectively etched. The second channel dielectric layer is then subject to further photolithographic process and etching steps to simultaneously form second channel and via openings in the pattern of the second channels and the vias. The photoresist is then stripped.

An optional thin adhesion layer is deposited on the second channel dielectric layer and lines the second channel and the via openings.

A barrier layer is then deposited on the adhesion layer and lines the adhesion layer in the second channel openings and the vias.

Again, for conductor materials such as copper and copper alloys, a seed layer is deposited by electroless deposition on the barrier layer and lines the barrier layer in the second channel openings and the vias.

A second conductor material is deposited on the seed layer and fills the second channel openings and the vias.

A CMP process is then used to remove the second conductor material, the seed layer, and the barrier layer above the second channel dielectric layer to form the first channels. When a dielectric layer is placed over the second channels as a final layer, it is called a "capping" layer and the "dual" damascene process is completed.

The layer may be processed further for placement of additional levels of channels and vias over it. Individual and multiple levels of single and dual damascene structures can be formed for single and multiple levels of channels and vias, which are collectively referred to as "interconnects".

The use of the single and dual damascene techniques eliminates metal etch and dielectric gap fill steps typically used in the metallization process. The elimination of metal etch steps is important as the semiconductor industry moves from aluminum (Al) to other metallization materials, such as copper, which are very difficult to etch.

The electromagnetic performance of conductor layers, such as copper, at various levels of integrated circuit interconnects is related to diffusion at the interfaces. This interfacial diffusion is a function of the surface mobility of the conductive atoms. Historically, copper in particular has exhibited thermally driven surface grain grooving. The extent or presence of grain grooving is a function and a result of surface diffusion of the copper atoms. The ability to be able to monitor copper grain boundaries and void formation under the capping layer which is normally in place would be an excellent metric for electromigration resistance. However, the capping layer renders optical and electron microscopy and atomic force microscopy problematical.

A solution to this problem has been long sought but has long eluded those skilled in the art.

DISCLOSURE OF THE INVENTION

The present invention provides a method for imaging and monitoring grain boundaries, nodules or extrusions, voids, and separations or delaminations in conductive layers under dielectric capping layers in integrated circuit interconnects. By using the transparency of dielectric materials to X-rays combined with the reflective nature of conductive metals to X-rays, X-ray imaging can be used to view the grain boundaries, nodules or extrusions, voids, and separations or delaminations in conductive layers under dielectric capping layers in integrated circuit interconnects as lower reflected intensity X-rays.

The present invention provides a method for imaging and monitoring grain boundaries, nodules or extrusions, voids, and separations or delaminations in conductive layers under dielectric capping layers in integrated circuit interconnects. By using the transparency of dielectric materials to X-rays combined with the reflective nature of conductive metals to X-rays, X-ray imaging can be used to view the grain boundaries, nodules or extrusions, voids, and separations or delaminations in conductive layers (hereinafter referred to as "features") under dielectric capping layers in integrated circuit interconnects as lower reflected intensity X-rays.

BRIEF DESCRIPTION OF THE DRAWINGS

FIG. 3 (PRIOR ART) is a top view of a conductive layers in its as-deposited state.

FIG. 4 (PRIOR ART) is a view of the conductive layers after annealing showing larger size grains and grain boundaries as they would appear under optical or scanning electron microscope (SEM) imaging;

FIG. 5 (PRIOR ART) is a view of the conductive layers with a dielectric capping layer deposited thereon;

FIG. 6 (PRIOR ART) is a view of the conductive layers after annealing with visible nodules and/or extrusions; and FIG. 7 is a view of the conductive layers after annealing and X-ray imaging with visible voids.

BEST MODE FOR CARRYING OUT THE INVENTION

Figure 1:
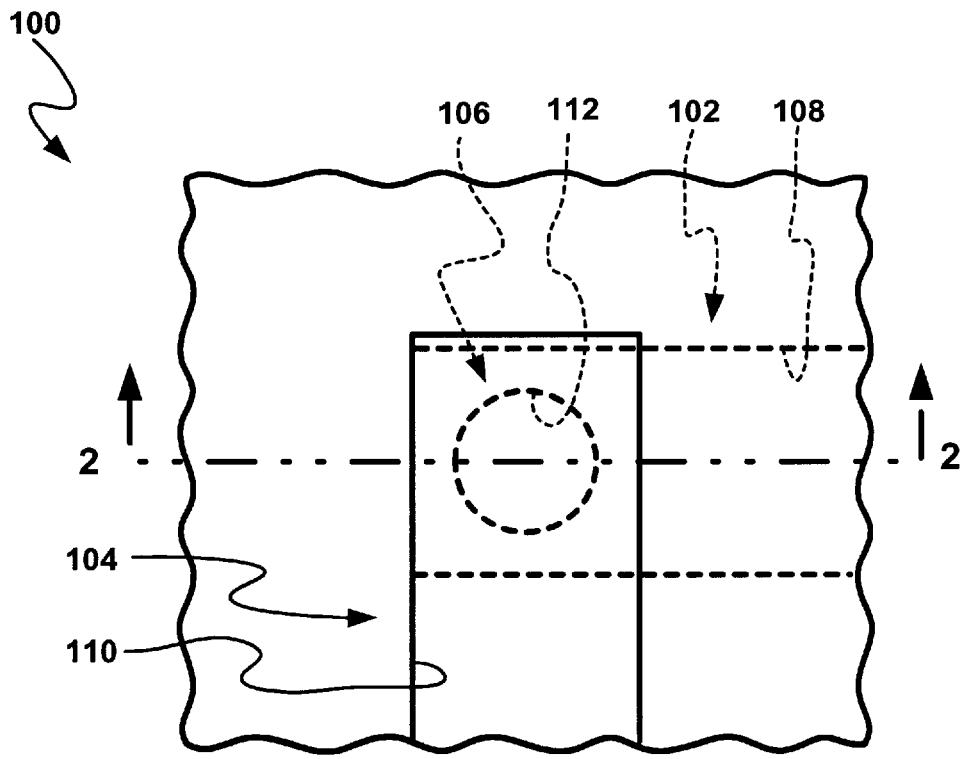
FIG. 1 (PRIOR ART) is a plan view of channels with a connecting via.

Referring now to FIG. 1 (PRIOR ART), therein is shown a plan view of a semiconductor wafer 100 with a silicon semiconductor substrate (not shown) having as interconnects first and second channels 102 and 104 connected by a via 106. The first and second channels 102 and 104 are respectively disposed in first and second channel dielectric layers 108 and 110. The via 106 is an integral part of the second channel 104 and is disposed in a via dielectric layer 112.

The term "horizontal" as used in herein is defined as a plane parallel to the conventional plane or surface of a wafer, such as the semiconductor wafer 100, regardless of the orientation of the wafer. The term "vertical" refers to a direction perpendicular to the horizontal as just defined. Terms, such as "on", "above", "below", "side" (as in "sidewall"), "higher", "lower", "over", and "under", are defined with respect to the horizontal plane.

Figure 2:
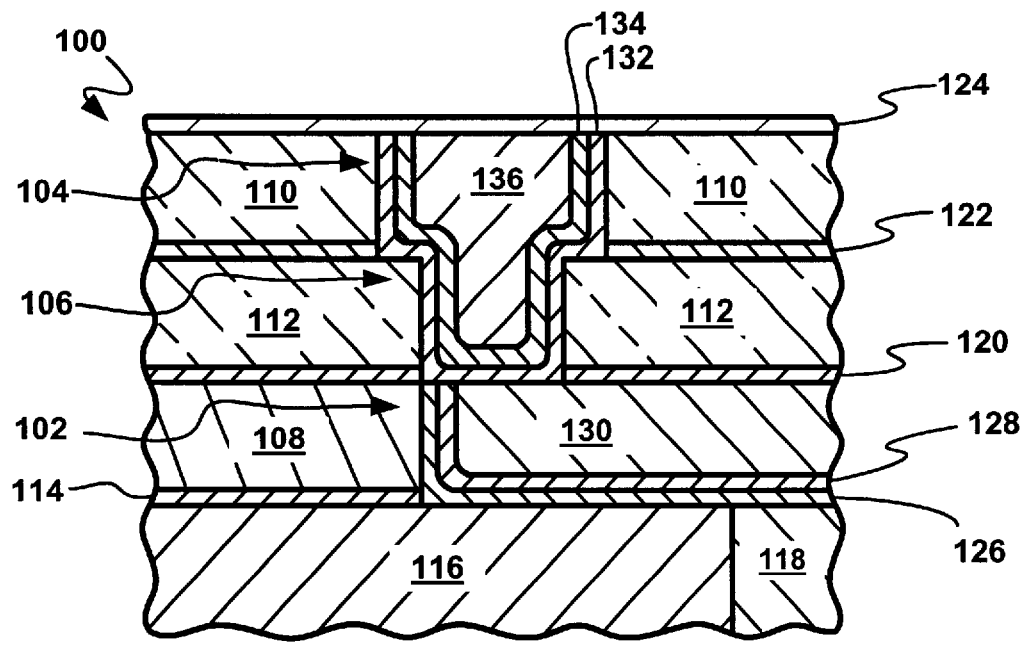
FIG. 2 (PRIOR ART) is a cross-section of FIG. 1 (PRIOR ART) along line 2—2.

Referring now to FIG. 2 (PRIOR ART), therein is shown a cross-section of FIG. 1 (PRIOR ART) along line 2—2. A portion of the first channel 102 is disposed in a first channel stop layer 114 and is on a device dielectric layer 116, which is on the silicon semiconductor substrate. Generally, metal contacts are formed in the device dielectric layer 116 to connect to an operative semiconductor device (not shown). This is represented by the contact of the first channel 102 with a semiconductor contact 118 embedded in the device dielectric layer 116. The various layers above the device dielectric layer 116 are sequentially: the first channel stop layer 114, the first channel dielectric layer 108, a via stop layer 120, the via dielectric layer 112, a second channel stop layer 122, the second channel dielectric layer 116, and a capping or next channel stop layer 124 (not shown in FIG. 1).

The first channel 102 includes a barrier layer 126, which could optionally be a combined adhesion and barrier layer, and a seed layer 128 around a conductor core 130. The second channel 104 and the via 106 include a barrier layer 132, which could also optionally be a combined adhesion and barrier layer, and a seed layer 134 around a conductor core 136. The barrier layers 126 and 132 are used to prevent diffusion of the conductor materials into the adjacent areas of the semiconductor device. The seed layers 128 and 134 form electrodes on which the conductor material of the conductor cores 130 and 136 is deposited. The seed layers 128 and 134 are of substantially the same conductor material as the conductor cores 130 and 136 and become part of the respective conductor cores 130 and 136 after the deposition.

In the past, for copper conductor material and seed layers, highly resistive diffusion barrier materials such as tantalum nitride (TaN), titanium nitride (TiN), or tungsten nitride (WN) are used as barrier materials to prevent diffusion Referring now to FIG. 3 (PRIOR ART), therein is shown a top view of a conductive layer 150, such as copper, in its as-deposited state. The conductive layer 150 shows grains 152 having grain boundaries 154.

Referring now to FIG. 4 (PRIOR ART), therein is shown the conductive layer 150 after annealing which shows larger size grains 162 and the grooving of larger grain boundaries 164 as they would appear under optical or scanning electron microscope (SEM) imaging. After annealing, nodules or extrusions 166 and voids 168 sometime form which may adversely affect the performance of the channels 102 or 104.

By implication, if the nodules or extrusions 166 and voids 168 appear in the channels 102 or 104, they are also probably present in the via 106 and will detrimentally affect performance of the integrated circuit.

Referring now to FIG. 5 (PRIOR ART), therein is shown the conductive layer 150 as deposited with a dielectric capping layer 170 of a material such as a silicon nitride or other dielectric material deposited over it. The grains 152 and the grain boundaries 154 of FIG. 3 (PRIOR ART) may be seen only slightly through the dielectric capping layer 170 as shapes 172. The exact configuration of the shapes 172 would be difficult to determine.

Referring now to FIG. 6 (PRIOR ART), therein is shown the conductive layer 150 after annealing. As with FIG. 4 (PRIOR ART), the annealing process will result in the larger size grains 162 having the grooving of the larger grain boundaries 164 which may be seen only slightly through the dielectric capping layer 170 as shapes 182. The exact configuration of the shapes 182 would be difficult to determine. The nodules and/or extrusions 166 will be visible as shapes 184, but the voids 168 would not be visible.

Referring now to FIG. 7, therein is shown the conductive layer 150 after annealing and X-ray imaging. X-ray imaging will show the larger size grains 162 and the grain boundaries 164 as darker areas through the dielectric capping layer 170. The nodules or extrusions 166 will be visible as will the voids 168 as darker. Further, separation or delamination 188 of the dielectric capping layer 170 from the conductive layer 150 can also be detected.

While it is not possible to directly image through the dielectric capping layer 170 by using optical or SEM imaging, it was discovered that X-rays could be used to penetrate the dielectric capping layer 170 and be reflected off of the conductive layer 150. The X-rays reflections from the nodules or extrusions 166 are of a lower intensity from the conductive layer 150 and reflections from the voids 168 and delaminations 188 are different from the reflections from both the nodules or extrusions 166 and the conductive layer 150.

The analysis of the X-ray image provides a metric for the analysis of the manufacturing process as well as conductive layer characteristics such as resistance to. electromigration which is a function of the number of grain boundaries.

As an added benefit, X-ray fluorescence spectra 190 from the grain boundaries 164 will permit identification of the elements at the grain boundaries 164 through the dielectric capping layer 170. This will allow analysis of the affect of different chemical elements and compounds on the grain structure.

In various embodiments, the barrier layers are of materials such as tantalum (Ta), titanium (Ti), tungsten (W), compounds thereof, and combinations thereof. The seed layers (where used) are of materials such as copper (Cu), gold (Au), silver (Ag), compounds thereof and combinations thereof with one or more of the above elements. The conductor cores with or without seed layers are of materials such as copper, aluminum (Al), gold, silver, compounds thereof, and combinations thereof. The dielectric layers are of dielectric materials such as silicon oxide ($SiO_x$), tetraethoxysilane (TEOS), borophosphosilicate (BPSG) glass, etc. with dielectric constants from 4.2 to 3.9 or low dielectric constant dielectric materials such as fluorinated tetraethoxysilane (FTEOS), hydrogen silsesquioxane (HSQ), benzocyclobutene (BCB), etc. with dielectric constants below 3.9. The stop layers and capping layers (where used) are of materials such as silicon nitride ($Si_xN_x$) or silicon oxynitride (SiON).

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations that fall within the spirit and scope of the included claims. All matters hitherto-fore set forth or shown in the accompanying drawings are to be interpreted in an illustrative and non-limiting sense.

The invention claimed is:

1. A method for monitoring a conductive layer under a dielectric layer comprising:

providing a conductive layer;

depositing a dielectric layer over the conductive layer;

annealing the conductive layer and the dielectric layer;

X-ray imaging the conductive layer and the dielectric layer;

using the reflected X-rays to determine features of the annealed conductive layer; and using the features as a metric for analysis of the conductive layer.

2. The method as claimed in claim 1 wherein using the features uses the reflected X-rays to determine the grain boundaries of the annealed conductive layer.

3. The method as claimed in claim 1 wherein using the features uses the reflected X-rays to determine voids.

4. The method as claimed in claim 1 wherein using the features uses the reflected X-rays to determine delamination of the dielectric capping layer from the conductive layer.

5. The method as claimed in claim 1 including using X-ray fluorescence for qualitative analysis of elements at the features.

6. The invention as claimed in claim 1 including using X-ray fluorescence for qualitative analysis of elements at grain boundaries of the annealed conductive layer.

7. The method as claimed in claim 1 wherein using the features as a metric determines the resistance of the electromigration.

8. A method for monitoring copper under a silicon nitride layer in an integrated circuit comprising:

providing a copper layer on the integrated circuit;

depositing a silicon nitride layer over the copper layer;

annealing the copper layer and the silicon nitride layer;

X-ray imaging the copper layer and the silicon nitride layer;

using the reflected X-rays to determine features of the annealed copper layer; and using the features as a metric for analysis of the copper layer.

9. The method as claimed in claim 8 wherein using the features uses the reflected X-rays to determine the grain boundaries of the annealed copper layer.

10. The method as claimed in claim 8 wherein using the features uses the reflected X-rays to determine void formation in the annealed copper layer.

11. The method as claimed in claim 8 wherein using the features uses the reflected X-rays to determine delamination of the silicon nitride layer from the annealed copper layer.

12. The method as claimed in claim 8 including using X-ray fluorescence for qualitative analysis of elements at the features.

13. The invention as claimed in claim 8 including using X-ray fluorescence for qualitative analysis of elements at grain boundaries of the annealed copper layer.

14. The method as claimed in claim 8 wherein using the features as a metric determines the resistance of the copper layer to electro-migration.

* * * * *

UNITED STATES PATENT AND TRADEMARK OFFICE
CERTIFICATE OF CORRECTION

PATENT NO.    : 6,541,286 B1
DATED         : April 1, 2003
INVENTOR(S)   : Bernard et al.

It is certified that error appears in the above-identified patent and that said Letters Patent is hereby corrected as shown below:

Column 3,
Line 33, delete the paragraph:
"The present invention provides a method for imaging and monitoring grain boundaries, nodules or extrusions, voids, and separations or delaminations in conductive layers under dielectric capping layers in integrated circuit interconnects. By using the transparency of dielectric materials to X-rays combined with the reflective nature of conductive metals to X-rays, X-ray imaging can be used to view the grain boundaries, nodules or extrusions, voids, and separations or delaminations in conductive layers under dielectric capping layers in integrated circuit interconnects as lower reflected intensity X-rays."

Column 3,
Line 43, insert two paragraphs:
-- The present invention still further provides a methods for a qualitative analysis of the elements at the grain boundaries by X-ray fluorescence.

The above and additional advantages of the present invention will become apparent to those skilled in the art from a reading of the following detailed description when taken in conjunction with the accompanying drawings. --

Column 4,
Line 37, delete "116" and insert -- 110 --

Column 5,
Line 41, delete "."

Signed and Sealed this

Twelfth Day of August, 2003

JAMES E. ROGAN
*Director of the United States Patent and Trademark Office*